Figure 1:
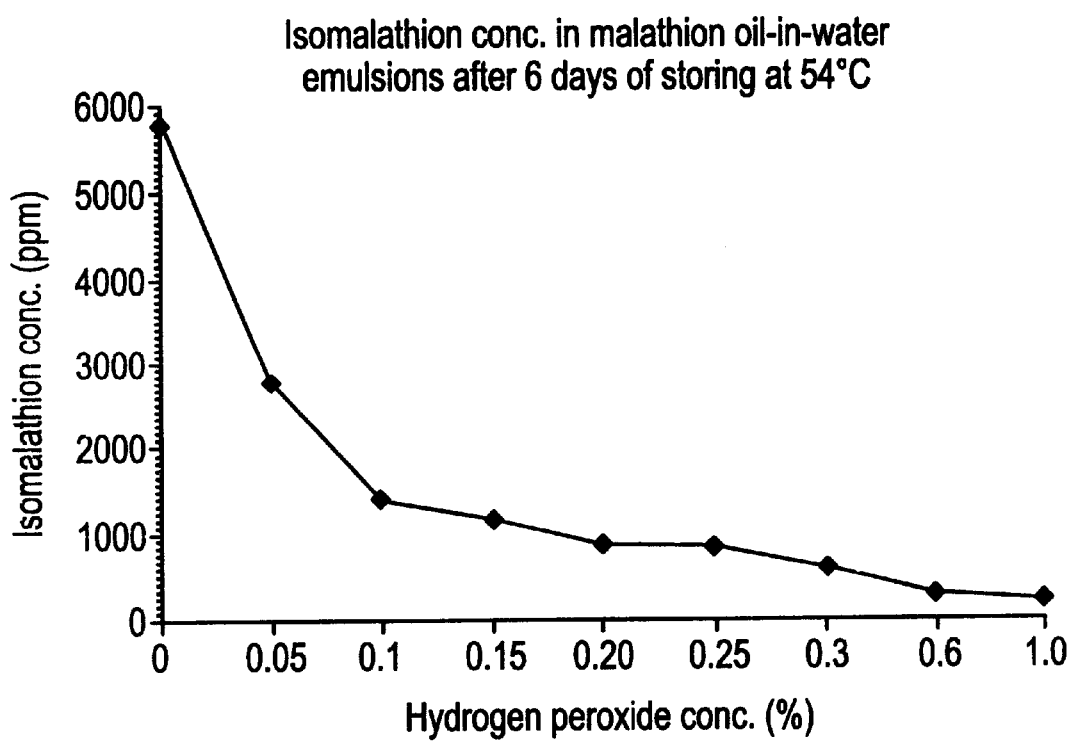

«12» United States Patent [19]

Pedersen

[11] Patent Number: 6,121,478
[45] Date of Patent: Sep. 19, 2000

[54] MALATHION OIL-IN-WATER EMULSION FORMULATIONS AND USE OF PEROXIDE IN SUCH FORMULATIONS

[75] Inventor: Morten Pedersen, Lemvig, Denmark

[73] Assignee: Cheminova Agro A/S, Harboor, Denmark

[21] Appl. No.: 09/250,612

[22] Filed: Feb. 17, 1999

Related U.S. Application Data

[63] Continuation of application No. PCT/DK97/00333, Aug. 19, 1997.

[51] Int. Cl.[7] ............................. C07F 9/165; A11N 57/12
[52] U.S. Cl. ................................................ 558/71; 558/180
[58] Field of Search ........................................ 558/71, 180

[56] References Cited

U.S. PATENT DOCUMENTS

| | | |
|---|---|---|
| 2,879,284 | 3/1959 | Divine et al. . |
| 2,962,521 | 11/1960 | Usui . |
| 3,314,851 | 4/1967 | Craig . |
| 3,714,301 | 1/1973 | Thomsen . |
| 4,263,136 | 4/1981 | Gagliardi et al. . |
| 4,851,217 | 7/1989 | Mente . |

FOREIGN PATENT DOCUMENTS

WO 94/10839  5/1994  European Pat. Off. .

OTHER PUBLICATIONS

C.K. Grätzel, et al., "Decomposition of Organophosphorus Compounds on Photoactivated $TiO_2$ Surfaces," *Journal of Molecular Catalysis*, vol. 60 (1990), pp. 375–387.

P. Aires, "Photochemical Degradation of Malathion in Aqueous Solutions," *J. Photochem. Photobiol. A: Chem.*, vol. 68 (1992), pp. 121–129.

*Primary Examiner*—Michael G. Ambrose
*Attorney, Agent, or Firm*—Smith, Gambrell & Russell, LLP

[57] ABSTRACT

Addition of an oxidation agent to completely or partially water-based organophosphate pesticide formulations or solid organophosphate pesticide formulations improves the chemical stability of the pesticide, minimizes formation of toxic isomeric compounds, and eliminates the development of mercaptan and sulfide smell.

11 Claims, 1 Drawing Sheet

Isomalathion conc. in malathion oil-in-water emulsions after 6 days of storing at 54°C

MALATHION OIL-IN-WATER EMULSION FORMULATIONS AND USE OF PEROXIDE IN SUCH FORMULATIONS

This application is a continuation of PCT/DK97/00333 filed Aug. 19, 1997, which application is relied upon and entirely incorporated herein by reference. Additionally, this application claims priority benefits based on Denmark Appln. No. 0877/96, which application also is relied upon and entirely incorporated herein by reference.

The present invention relates to malathion oil-in-water emulsion formulations comprising malathion as active ingredient and the usual formulation, carrier and auxiliary agents. The invention further relates to the use of one or more peroxide(s) as an additive to malathion oil-in-water formulations for reducing the contents of isomalathion therein without a simultaneous reduction in the chemical stability of malathion present therein.

It is well known that organophosphate pesticides, e.g. malathion, methyl parathion, dimethoate and chlorpyrifos when stored carry or develop an obnoxious odour, which for the major part is probably due to the formation of decomposition products of the mercaptan and sulphide type.

Inhibition of the development or removal of the unpleasant odour in organophosphate pesticides or from organic solvent-based pesticide formulations may at least partially be achieved by adding small amounts of oxidation agent, e.g. peroxides, nitrites, nitrogen oxides or ozone, to the pesticides (U.S. Pat. No. 3,714,301; U.S. Pat. No. 2,962,521; U.S. Pat. No. 2,879,284; GB 960,013 and WO97/25076). The oxidation agents oxidize the unpleasantly smelling mercaptans and sulphides into odourless compounds.

According to U.S. Pat. No. 4,851,217 an addition of urea to oil-in-water emulsion formulations of organophosphate pesticides will ameliorate the malodor problem inherent in such formulations and also physically/chemically stabilize the emulsion. But urea does not stabilize the proper active compound, such as malathion.

It is known to use peroxides for removal of bad odour from sewage containing organophosphate, e.g. malathion (U.S. Pat. No. 4,263,136). The patent leaves the impression that malathion in the sewage water may be decomposed in connection with the peroxide treatment.

Problems of destabilizing organophosphate pesticides by adding oxidation agents are described in U.S. Pat. No. 3,714,301 and U.S. Pat. No. 2,879,284. In U.S. Pat. No. 3,714,301 it is stated that the known deodorizing treatment of organic thiophosphate products with peroxides or ozone in many cases resulted in the sulphur atom being replaced with an oxygen atom (i.e. forming oxone compounds such as paraoxon from parathion and malaoxon from malathion). In U.S. Pat. No. 3,314,851 it is mentioned how addition of ozone or hydrogen peroxide and possibly a catalyst to a parathion oil-in-water emulsion leads to formation of paraoxon. The conversion of parathion to paraoxon and, possibly because the product is present as an oil-in-water emulsion, implicates a reduced toxicity for mammals of said product.

According to said reference, a similar treatment of a malathion oil-in-water emulsion with hydrogen peroxide leads to formation of malaoxon which, however, toxicologically is unwanted. Malaoxon is considerably more toxic for mammals than malathion, the oral $LD_{50}$ value for rats being 158 mg/kg for malaoxon but 5500 mg/kg for malathion (NIOSH, Registry of Toxic Effects of Chemical Substances, 1981–1982, and Kyosh, S. R., Project No. 851341D/CHV/33/AC, 1986).

Grätzel, C. K. et al. (J.Mol.Catal., 60(1990) 375–378) proved that addition of oxidation agent, e.g. hydrogen peroxide, to aqueous organophosphate pesticide dispersions of e.g. malathion and parathion increased the decomposition of the pesticide considerably, i.a. on account of a direct oxidation of the compounds.

Jensen-Holm, J. (Ugeskr. Laeg. (Doctors' Weekly) 143 (48) (1981) 3206–3211) described the catalytic effect of hydrogen peroxide on the decomposition of organophosphate pesticides in aqueous waste products.

Destruction of organophosphate pesticides in waste water by means of oxidation agents is likewise described by Lion, C. et al. (Bull.Soc. Chim.Belg. 103(1994) 115–118), Egli, S. et al. (Chem.Oxid. 1992 (1994) 264–277), Hu, K. et al. (Huanjing Huaxue 9(1990) 13–19) and Gomaa, H. M. et al. (Advan.Chem.Ser. (1972), 111, Fate of Org. Pestic. in the Aquatic Environ., 189–209).

According to Pilar Aires et al. (J.Photochem. Photobiol. A: Chem. 68(1992) 121–129) the presence of only 0,6% hydrogen peroxide in an aqueous malathion solution increased the decomposition of pesticide by a factor 10, which meant that practically all malathion had been decomposed in the course of a few days of storing at room temperature, even though pH was near optimum for the stability of malathion.

In contrast to the chemical destabilization of malathion which as stated above occurs when peroxides or ozone are added to aqueous malathion products, it is according to U.S. Pat. No. 3,714,301, U.S. Pat. No. 2,962,521 and U.S. Pat. No. 2,879,284 possible to obtain a deodorization (primary) and, further, a stabilization against a development of new mercaptane and sulphide smell, when ozone, peroxide or nitrite are added to malathion products, if any aqueous phase present are removed from the active agent malathion immediately after said addition of oxidation agent. If any aqueous phase remains with the active agent the above mentioned decomposition reactions will initiate. A subsequent drying of malathion, possibly under vacuum, is accordingly elaborated upon in U.S. Pat. No. 3,714,301 and U.S. Pat. No. 2,962,521. If malathion is not effectively dried the formation of the isomer isomalathion will entail toxicological problems, isomalathion being more toxic to mammals than malathion proper.

The above mentioned organophosphate pesticides are often used as solutions in organic solvent. The solutions are diluted with water immediately before spraying. For both environmental reasons and for reasons concerning the working environment there is a wide-spread desire to use, instead of solutions of pesticides in organic solvent, oil-in-water emulsion formulations of the pesticides without any content of organic solvent.

The chemical stability of malathion and its toxicity properties are considerably worsened by the presence of water in formulations thereof. The formation of isomalathion in aqueous malathion formulations is an example of decomposition of an organophosphate pesticide to an isomer which is more toxic than the pesticide itself. The problem is thus not only that isomalathion per se is the most toxic compound, but further that iso compounds are to a considerable degree known for potentiating the inherent toxicity of the active agents on humans and animals.

Consequently, both the initial content and the formation of iso-malathion in malathion formulations are to be limited as much as possible; moreover, authorities do only allow very limited concentrations of the toxic iso-malathion in commercial malathion formulations.

It is possible to a certain degree to limit the conversion of malathion to iso-malathion by adequately choosing auxiliary compounds such as e.g. carriers and emulsifying agents, and by adequately choosing the type of packaging, and the value of pH in the formulations. Thus, malathion oil-in-water formulations are mentioned in U.S. Pat. No. 4,851,217 and WO 94/10839. In both publications malathion oil-in-water formulation are said to possess physical-chemical stability, and U.S. Pat. No. 4,851,217 further states that addition of urea, besides of the physical-chemical stabilization of the emulsion also decreases an evolution of mercaptane and sulphide stench.

However, a formation of iso-malathion when storing such emulsions has not been investigated. If oil-in-water emulsions of malathion are prepared as described in U.S. Pat. No. 4,851,217 and WO 94/10839, unacceptable amounts of iso-malathion are formed during their storage. This formation is found even if premium grade malathion (i.e. malathion treated with peroxide or nitrite according to U.S. Pat. No. 2,879,284, U.S. Pat. No. 2,962,521 or U.S. Pat. No. 3,714,521 and then (vacuum-)dried is used in the preparations.

Methods for effectively reducing the formation of iso-malathion in malathion oil-in-water emulsion formulations are to our knowledge not described in the literature.

It has most surprisingly been found that addition of peroxides to malathion oil-in-water emulsion formulations considerably reduces the concentration of the toxic isomeric compound isomalathion, even after a prolonged storage at elevated temperatures. Likewize, it has surprisingly been found that said addition of peroxides does not impair the chemical stability of malathion as it would be expected in view of the above (U.S. Pat. No. 4,263,136; U.S. Pat. No. 3,714,301; U.S. Pat. No. 2,879,284; J.Mol: Catal. 60(1990) 375–387; Ugeskr.Laeg. (Doctor's Weekly) 143(48) (1981) 3206–3211; Bull.Soc.Chim.Belg. 103(1994) 115–118; Chem.Oxid. 1992(1994) 264–267; Huanjing Auaxue 9(1980) 13–19; Advan.Chem:Ser. (1972) 111, Fate of Org. Pesic. in the Aquatic Environ. 189–209; J.Photochem.Photobiol. A: Chem. 68(1992) 121–129). Moreover, especially U.S. Pat. No. 3,314,851 should be mentioned, according to which even a short time treatment of water-emulgated parathion or malathion with peroxide or ozone leads to formation of paraoxon/malaoxon, respectively.

Accordingly, the malathion oil-in-water emulsion formulations of the invention are characterized in that to the formulations is added 0.01–10, preferably 0.05–3 and in particular 0.3–1 percentage by weight, of one or more peroxide(s).

In the use according to the invention the above stated amounts of peroxide(s) are employed.

Said addition will reduce the formation of iso-malathion to toxicologically acceptable values.

If the reduction of the contents of isomalathion in malathion oil-in-water emulsion formulations prompted by the inventive addition of peroxide(s) to such formulations was due to the same mechanism as by the removal of smell from technical malathion by an oxidation agent, it should be expected that addition of nitrite to the formulations would also lead to formulations with preferred properties. However, an addition of nitrite to malathion oil-in-water formulations leads to the formation of a considerable amount of nitric fumes which are toxic and of an evil stench. Thus, it is not possible for the skilled man from the disclosures of U.S. Pat. Nos. 3,714,301; 2,962,521; 2,879,284; and 3,314,851 to conclude how the auxiliary compounds nitrite and peroxide will influence the properties of malathion oil-in-water emulsion formulations.

Autooxidation of peroxide into water and oxygen may limit the effect of the peroxide on the content of isomalathion in malathion oil-in-water emulsion formulations. The autooxidation may, however, be considerably limited by addition of stabilizing agents which stabilize the peroxide without limiting its effect on the formation of the toxic isomalathion. Examples of peroxide stabilizing agents are e.g. EDTA, salicylic acid, propylgallate, acetanilide, 8-hydroxyquinoline, phenacetin and mixtures thereof.

In malathion oil-in-water emulsion formulations it may be advantageous to use a combination of peroxides with different solubilities in the phases and different distribution coefficients between the phases.

The addition of peroxide(s), alone or in combination with peroxide stabilizing agents, makes possible a development of malathion oil-in-water emulsion formulations with an acceptable low content of isomalathion.

The malathion oil-in-water emulsion formulations according to the invention may besides of malathion also contain one or more pesticides of a different type.

The invention will now be further illustrated by the following examples. The concentrations of pesticides and decomposition products thereof were determined by gas and/or liquid chromatography and NMR spectroscopy.

EXAMPLE 1

Malathion 40% by weight oil-in-water emulsions were prepared lege artis using an optimal combination of emulgators. The stirring velocity during the emulsion formation was regulated such that the volume-surface middle diameter was 10–12 μm. A suitable viscosity was obtained by addition of viscosity increasing compounds. The value of pH was regulated so as to obtain optimal malathion stability.

The concentration of hydrogen peroxide in the emulsions was varied. The contents of isomalathion was analytically determined after storing of the formulations for 6 and 14 days at 54° C. (accelerated storing test). Likewise, the contents of malathion was analytically determined before and after storing.

FIG. 1 shows the relationship between initial hydrogen peroxide concentration and isomalathion concentration after 6 days of storing. A considerable reduction of the isomalathion concentration was obtained by addition of hydrogen peroxide. A pronounced reduction of the isomalathion concentration is obtained even after 14 days of storing at 54° C.

It appears from Table 1 (below) that the chemical stability during a storing test at 54° C. is improved by the addition of hydrogen peroxide.

TABLE 1

Decomposition of malathion in 40% by weight oil-in-water emulsions at storing for 14 days at 54° C.

| | | | |
|---|---|---|---|
| % hydrogen peroxide in formulation | 0 | 0,1 | 0,3 |
| % malathion decomposed relative to initial content | 7,0 | 3,4 | 1,4 |

EXAMPLE 2

In selected malathion oil-in-water formulations the chemical stability of malathion and the formation of isomalathion was investigated during storing of said formulations for months at 23° C. The results appear from Table 2 (below). Addition of hydrogen peroxide considerably reduces the isomalathion concentration and improves the chemical stability of malathion.

TABLE 2

Decomposition ot malathion, and isomalathion concentration in malathion 40% by weight oil-in-water emulsions when stored for 4 months at 23° C.

| | | | |
|---|---|---|---|
| % hydrogen peroxide in formulation | 0 | 0,1 | 0,3 |
| % malathion decomposed relative to initial content | 1,4 | 0,73 | 0,24 |
| pprn isomalathion after storing | 1404 | 217 | <10 |

EXAMPLE 3

Methyl parathion 40% by weight oil-in-water emulsions were prepared in accordance with the same method and by use of the same auxiliary compounds as mentioned in Example 1.

Formulations without hydrogen peroxide and with 0,3% hydrogen peroxide were prepared; to some of these formulations was added 5 mg/ml isomalathion.

The concentrations of isomethyl parathion and isomalathion were determined before and after storing at 54° C. for 6 days or at 23° C. for 6 days. The results in Table 3 (below) show that the function of hydrogen peroxide in reducing the concentration of the isomeric compound is not to increase the rate of decomposition of the proper isomeric compound (isomalathion) but, in contrary, to inhibit the transformation of pesticide (methyl parathion) into an isomeric compound (isomethyl parathion).

TABLE 3

Methyl parathion 40% by weight oil-in-water emulsions with different initial contents of hydrogen peroxide and isomalathion. The concentrations of isomethyl parathion and isomalathion, respectively, are shown after storing the formulations for 6 days at 23° C./54° C.

| Initial Composition of formulation | (6 d. 23° C.) isomethyl parathion (ppm) | (6 d. 23° C.) isomalathion(IM) (ppm) | (6 d. 54° C.) isomethyl parathion (ppm) | (6 d. 54° C.) isomalathion(IM) (ppm) |
|---|---|---|---|---|
| 0% H$_2$O$_2$ 0% IM | 2700 | <10 | 23400 | <30 |
| 0% H$_2$O$_2$ 0,5% IM | 4600 | 5591 | 17500 | 2153 |
| 0,3% H$_2$O$_2$ 0% IM | 2100 | <10 | 8500 | <30 |
| 0,3% H$_2$O$_2$ 0,5% IM | 3500 | 4352 | 6600 | 2793 |

EXAMPLE 4

To premium grade malathion (treated as prescribed in U.S. Pat. No. 3,714,301) and technical malathion was added up to 1% of a peroxide; said peroxide being either hydrogen peroxide, benzoyl peroxide or tert-butyl peroxide. Samples of premium grade malathion and technical malathion with various concentrations of said peroxides and reference samples of premium grade malathion and technical malathion were stored in 14 days at 54° C. It was found that addition of an inorganic or organic peroxide to premium grade malathion and technical malathion had no influence on the concentration of isomalathion in the samples after storage and that the contents of iso-malathion in the samples with peroxide were the same as in the reference samples, viz. 0,1%.

The reduction of formation of isomalathion by peroxides is unique for malathion oil-in-water emulsion formulations. The reasons for the lack of influence by peroxides on the concentration of isomalathion after storage of premium grade malathion and technical malathion could be that peroxide stabilizes isomalathion formed in the pure active compound. The above Example 3 shows that addition of peroxide to a malathion oil-in-water emulsion does not stabilize produced isomalathion. The presence of peroxide in the emulsion does not change the rate of decomposition for isomalathion.

EXAMPLE 5

Malathion 65% and 40% by weight oil-in-water emulsions were prepared as described in U.S. Pat. No. 4,851,217 using Pluronic as emulsifyer; and 10% by weight urea, being a stabilizing agent according to said patent, was added to some of these emulsions. Furthermore, selected formulations were added with hydrogen peroxide. Table 4 (below) shows the test results therewith.

TABLE 4

Concentration of isomalathion in malathion oil-in-water emulsions with Pluronic, urea and hydrogen peroxide after storage in 6 and 14 days at 54° C.

| | | | ppm isomalathion | | |
|---|---|---|---|---|---|
| % malathion | % urea | % H$_2$O$_2$ | initially | 6 d. at 54° C. | 14 d. at 54° C. |
| 40 | — | 0,3 | 194 | 29 | 114 |
| 40 | 10 | — | 495 | 2900 | 11700 |
| 40 | 10 | 0,3 | 196 | 642 | 7700 |
| 40 | — | — | 200 | 2895 | 12593 |
| 65 | 10 | — | 1200 | 18900 | — |
| 65 | 10 | 0,3 | 317 | 1400 | — |

Example 5 shows that addition of urea which according to U.S. Pat. No. 4,851,217 should increase the emulsion stability and impede a development of mercaptane and sulphide smell, does not lower the concentration of isomalathion after storage, but rather the opposite. Addition of hydrogen peroxide gives (see Table 4) an effective reduction in the concentration of iso-malathion after storage, and the according to said us patent stabilizing effect of urea on malathion oil-in-water emulsion formulations is evidently of another type than the reduction in the concentration of iso-malathion obtained by an addition of hydrogen peroxide.

What is claimed is:

1. A malathion oil-in-water formulation comprising malathion, at least one of a carrier and an auxiliary agent, and 0.01 to 10 percent by weight of at least one peroxide.

2. The formulation according to claim 1 containing 0.05 to 3 percent by weight of at least one peroxide.

3. The formulation according to claim 1 containing 0.3 to 1 percent by weight of at least one peroxide.

4. The formulation according to claim 1, wherein the peroxide is hydrogen peroxide.

5. The formulation according to claim 1, wherein the peroxide or peroxides are stabilized against auto-oxidation by including a stabilizing agent.

6. The formulation according to claim 5, wherein the stabilizing agent is a member selected from the group consisting of: EDTA, salicylic acid, propyl gallate, acetanilide, 8-hydroxyquinoline, phenacetin, and mixtures thereof.

7. A process for reducing the content of any isomalathion by adding 0.05 to 3 percent by weight of at least one peroxide as an additive to a malathion oil-in-water formulation without a simultaneous reduction in the chemical stability of malathion present therein.

8. A malathion oil-in-water formulation comprising malathion, at least one of a carrier and an auxiliary agent, and 0.01 to 10 percent by weight of at least one peroxide, wherein the peroxide or peroxides are stabilized against auto-oxidation by including a stabilizing agent.

9. The formulation according to claim 8 containing 0.05 to 3 percent by weight of at least one peroxide.

10. The formulation according to claim 8 containing 0.3 to 1 percent by weight of at least one peroxide.

11. The formulation according to claim 8, wherein the stabilizing agent is a member selected from the group consisting of: EDTA, salicylic acid, propyl gallate, acetanilide, 8-hydroxyquinoline, phenacetin, and mixtures thereof.

* * * * *